United States Patent [19]

Larsson

[11] Patent Number: 4,597,096
[45] Date of Patent: Jun. 24, 1986

[54] MULTITUBE COLLIMATOR FOR FOR INSTANCE SCINTILLATION CAMERA

[76] Inventor: Agne Larsson, Barytongatan 24, Västra Frölunda, Sweden, 421 38

[21] Appl. No.: 639,530

[22] PCT Filed: Sep. 9, 1981

[86] PCT No.: PCT/SE81/00251
§ 371 Date: May 7, 1982
§ 102(e) Date: May 7, 1982

[87] PCT Pub. No.: WO82/00897
PCT Pub. Date: Mar. 18, 1982

Related U.S. Application Data

[63] Continuation of Ser. No. 380,672, May 7, 1982, abandoned.

[30] Foreign Application Priority Data

Sep. 10, 1980 [SE] Sweden .................................. 8006301

[51] Int. Cl.⁴ ............................................. G03B 41/16
[52] U.S. Cl. ...................................... 378/149; 378/150
[58] Field of Search ........................... 378/149, 150; 250/505.1

[56] References Cited

U.S. PATENT DOCUMENTS

| | | | |
|---|---|---|---|
| 2,659,017 | 11/1953 | Bartow | 378/149 |
| 2,665,387 | 1/1954 | Bartow | 378/149 |
| 3,790,782 | 2/1974 | Inoue | 378/149 |
| 3,805,081 | 4/1974 | Barthel | 378/150 |
| 3,997,794 | 12/1976 | York | 378/149 |
| 4,118,632 | 10/1978 | Luig | 378/150 |

Primary Examiner—Craig E. Church

[57] ABSTRACT

A multitube collimator for a camera, especially a scintillation camera, whose sensitivity and resolving power may be varied by changing the length, slope, dimension or shape of the tubes (10). This is achieved by that the grid at least at two opposed limiting sides is surrounded by guiding means (11) which are arranged to, by parallel movement and/or by moving towards or apart from each other, influence the collimator tubes (10) collectively referred to the positions of the tubes relative to the guiding means (11) and/or the dimension of the tubes in the longitudinal and/or transverse direction.

3 Claims, 24 Drawing Figures

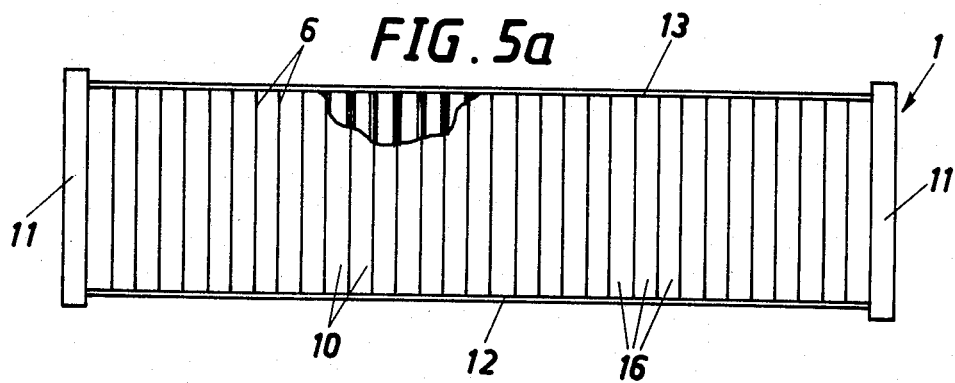
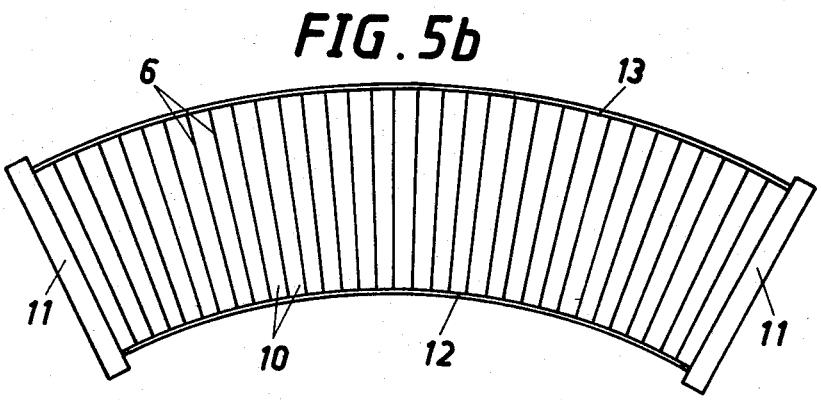

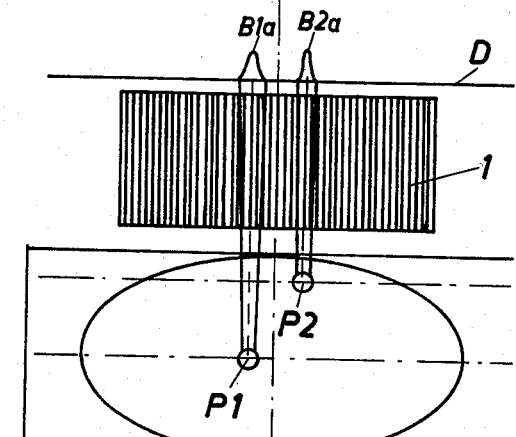
FIG. 6a
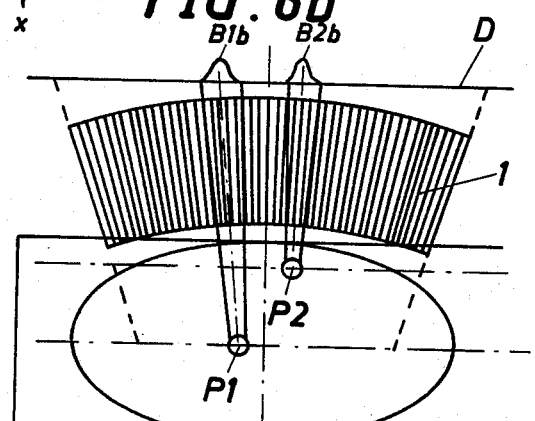
FIG. 6b
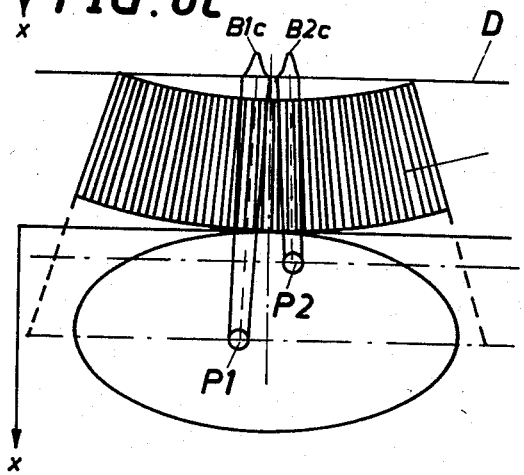
FIG. 6c
FIG. 7
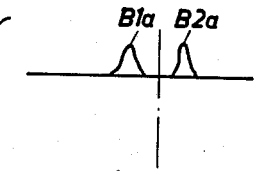
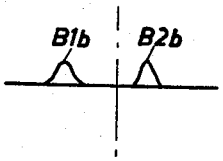
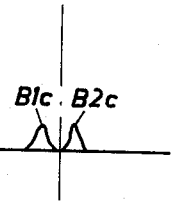
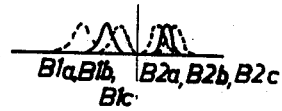
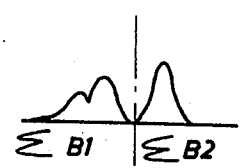

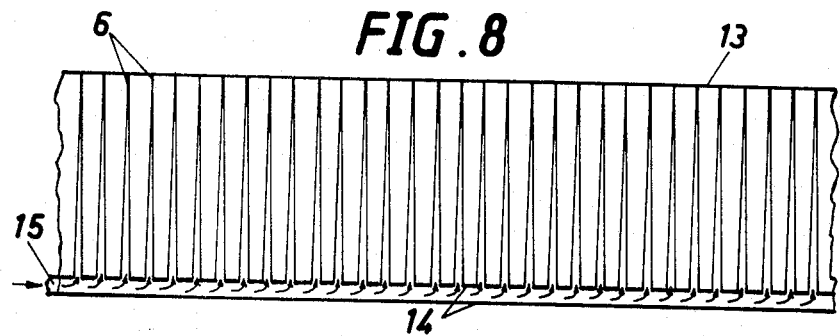
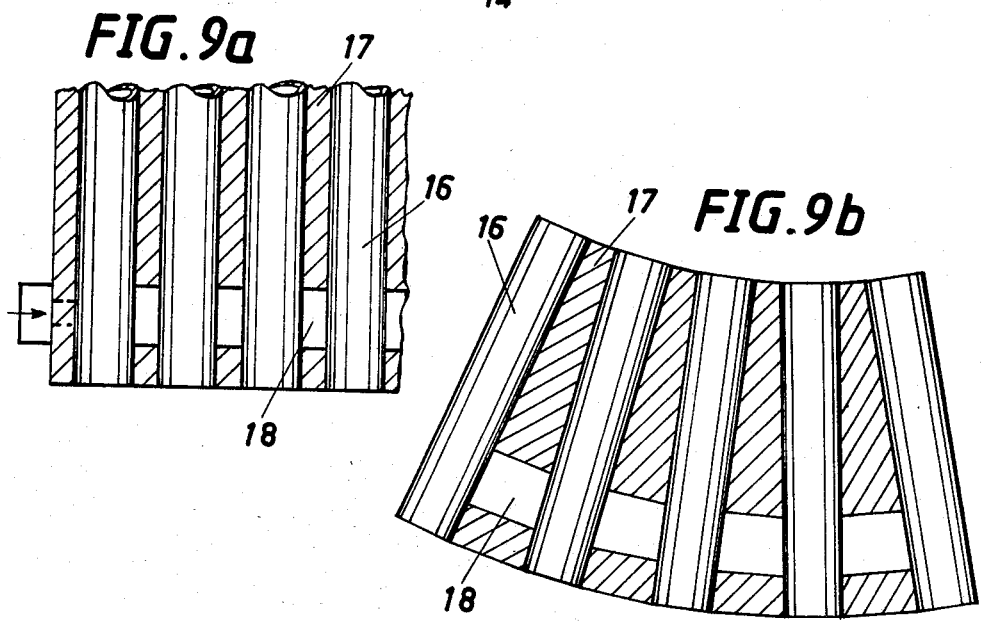
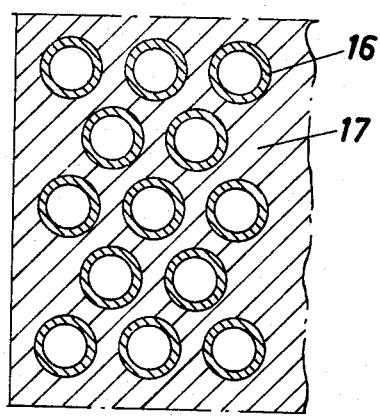

MULTITUBE COLLIMATOR FOR FOR INSTANCE SCINTILLATION CAMERA

This application is a continuation of application Ser. No. 380,672, filed May 7, 1982, now abandoned.

BACKGROUND OF THE INVENTION

The present invention relates to a multitube collimator or the like to be placed between a radiation source and a radiation sensitive medium, for example for scintillation cameras, comprising a grid the walls of which are made of a radiation absorbing material and being moveable for setting in different angular positions.

During the last decade radionucelides (radioactive isotopes) have become more and more important as a facility in medicine when diagnosing and mapping the distribution of unhealthy processes in different organs. This depends partly on the fact that the number of available short duration radionucleides and radioactive pharmaseptica has increased and partly on the fact that progress has carried about effective instruments for the detection and registration of the gamma radiation from the organ or organs which has/have enriched the radionucleides which are delivered to the patient. One such instrument is the so called scintillation camera, often called the gamma camera, which was invented by Anger at the end of the fifties, and which is today spread in a great number all over the world.

A gamma camera is a relatively expensive instrument that in a basic version costs about 500,000 swedish kronor. Additionally, there is the cost of the surrounding equipment to which the so called collimators belong. A modern multitube collimator costs about 20,000 swedish kronor. In order to reach the best possible examination results in a given situation it is necessary to have a number of different colimators at hand.

The expensiveness and the possibilities to reach high quality examination results with the gamma camera generally lead to an effort to keep the frequency of use at a high level. Frequent change of collimators which thus is a nessecity for making use of the potential possibilities of the gamma camera is a circumstance that strongly contributes to keep the frequency of use at a low level or to decrease it.

The collimator is the image making element in a gamma camera. The geometric distance of resolution and the sensitivity are characteristic properties of a gamma camera. The geometric distance of resolution of the gamma camera is a measure of the accuracy that the collimator contributes to the number of details in the image that reproduces a certain distrubution of radionucleides. The sensitivity of the collimator is a measure of the transparency for gamma photons from a source of radionucleides.

The system distance of resolution of the gamma camera, which is a measure of the total resolving power of the gamma camera system, is a function of the internal geometric distance of resolution of the gamma camera and the geometric distance of resolution of the collimator. The internal distance of resolution of the gamma camera which is the minimum possible distance between two well collimated photon rays when they are separated in the image of the gamma camera is in modern gamma cameras of the same order as the geometrical distance of resolution of the collimator when the radionuclide source is near to the collimator.

For a parallel tube collimator the geometrical distance of resolution is inversely proportional to the length of the tube.

For a converging multi tube collimator, which causes a reduced wiew range, the geometrical distance of resolution is of the same order as for a parallel tube collimator. The influence of the internal distance of resolution is however reduced by increasing convergency. The sensitivity is larger than for a parallel tube collimator.

A collimator may also be divergent, which leads to a larger field of wiew, but to a reduced resolving power.

The system distance of resolution of the gamma camera is strongly influenced by the distance of resolution of the collimator.

The sensitivity of the collimator is strongly influenced by the geometrical design of the tubes, i.e. their diameter and length and the wall thickness and by the slope of the tubes.

SUMMARY OF THE INVENTION

The object of the invention is to develope a collimator whose resolving power and sensitivity may be varied. This is achieved by using a grid that at least at two opposed limiting sides is surrounded by guiding means (11) which are arranged to, by parallel movement and/or by moving towards or apart from each other, influence the collimator tubes (10) collectively refered to the positions of the tubes relative to the guiding means (11) and/or the dimension of the tubes in the longitudinal and/or transverse direction.

DESCRIPTION OF THE DRAWINGS

The invention will in the following be described in more detail with reference to some of the embodiments described in the enclosed drawings.

FIGS. 5a-5b show a collimator which may be changed from a parallel tube collimator to a collimator with converging or diverging tubes respectively in two different positions.

FIGS. 6a, 6b and 6c visualize how a change of a parallel tube to a converging or diverging collimator respectively affects the positions of the the image points for two objects in different object planes.

FIG. 7 visualizes the result of a summation of the detected intensity of the image points of FIG. 6.

FIG. 8 shows another embodiment of a collimator in which a shape change of the collimator tubes may take place.

FIG. 9 is a vertical cut through another embodiment of collimator according to the invention.

FIG. 9b is a vertical cut through the same collimator in another position.

FIG. 10 is a cross cut through the same collimator.

DESCRIPTION OF EMBODIMENTS

Figure 1:
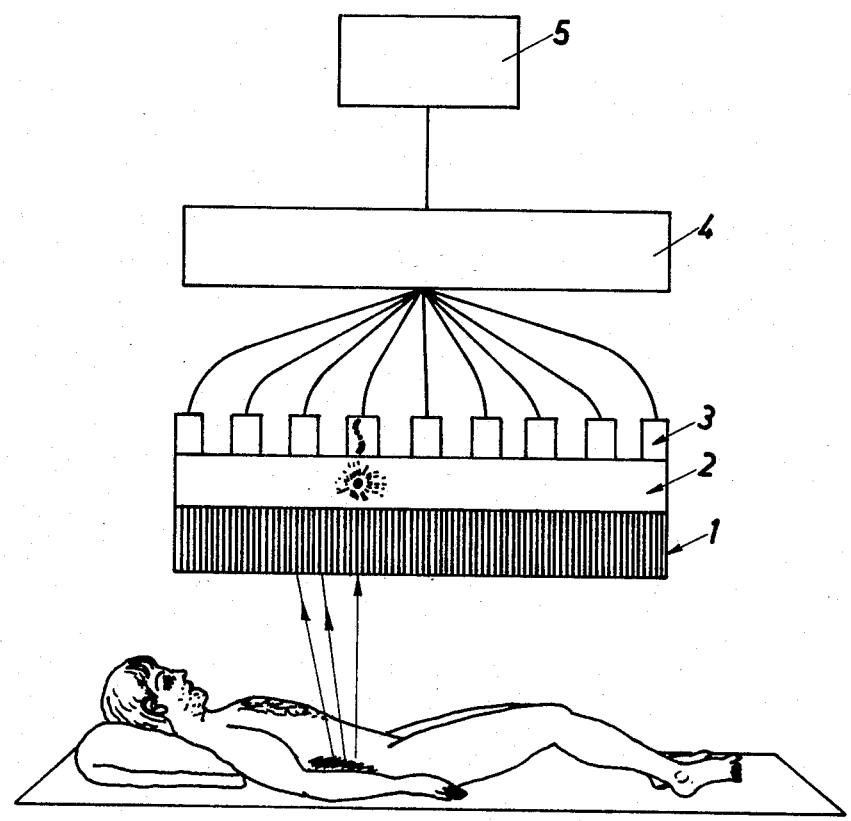
FIG. 1 shows in schematic presentation the design of a gamma camera.

A scintillation camera or gamma camera works with reference to FIG. 1 principally in the following way. A sample that is labelled with a radioactive isotope is injected into the patient, and the sample is chosen so that it is enriched in the organ under examination. Gamma rays i.e. photons are emitted from the sample that reach a multi tube collimator 1 which only transmits photons propagating parallel to the tubes. Photones propagating at other angles are absorbed by the walls of the collimator 1. Photons that reach the collimator 1 reach a detector 2, i.e. a scintillation crystal, which scintillates (emitts light flashes) when the photons are absorbed in it. The light flashes are detected by photomultipliers 3, in which they are converted into electrical pulses. These are registered by a registration device for example a computer 4, that assorts the pulses and delivers a picture of how the injected sample is distributed in the examined organ. By making such images from many different angles it is possible to deliver a three dimentional representation of the examined organ with help of suitable data programs. From the three dimentional representation it is possible to make section pictures of the organ with help of the dator. The section pictures are presented on a screen 5.

In order to utilize the potential possibilities of the gamma camera, i.e. to achieve an increased sensitivity, resolving power and a desired effective area of examination it has so far been necessary to frequently change collimators. A number of collimators with different geometric shape and/or different length are comersially available. These collimators are of a large size and are very heavy (the partitions are made of lead). The changing of collimators is thus a very complicated procedure.

With the help of the device according to the invention it is possible to achieve the desired sensitivity and resolving power and a desired area of examination by using only one collimator. In this way the quality of every single examination may be kept at a high level and, simultaneously, the total time consumtion for every single examination may be reduced to a minimum. Disregarding the purely economical advantage that it is possible to carry out several examinations per gamma camera every day, these advantages are of great value for the patient since they contribute to increase the diagnostical accuracy and to make the examination as careful as possible.

Figure 2A:
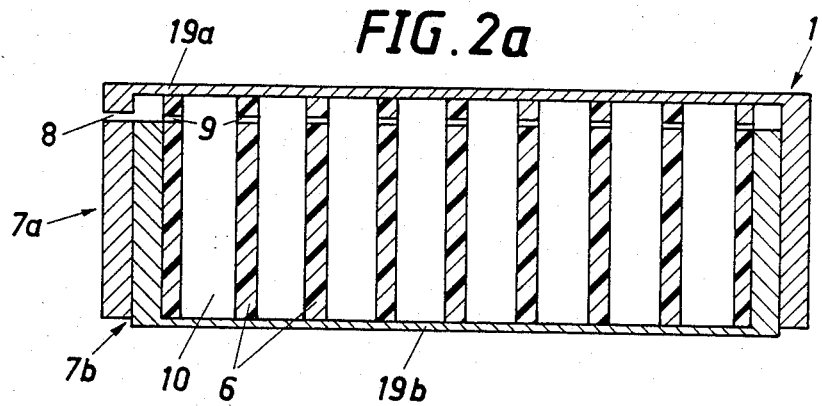
FIG. 2 is a schematic cut through an embodiment of a collimator according to the invention.
FIG. 2b is a cut through the same collimator as in FIG. 2a, but in this case an increased length of the walls is achieved.
Figure 2B:
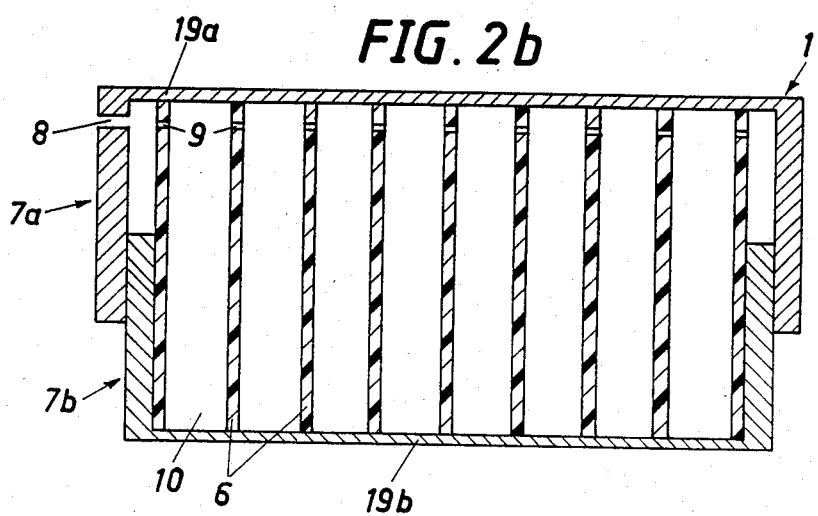

With reference to the embodiment shown in FIGS. 2a and 2b a collimator device, in which the length of the tubes and thereby the resolving power and the sensitivity of the collimator may be varied, may work in the following way.

The partition walls 6 of the collimator tubes consist of an elastic material that must have the property to very effectively absorb gamma photons. One material that fulfils this demand is for instance rubber with an admix of some heavy metal like lead, tungsten or tantalum.

The end surfaces of the walls 6 are fixed to the bottoms 19a and 19b respectively of two cans 7a and 7b which are telescopically insertable into each other. The first can 7a is fixed to the detector head of the gamma camera and its bottom 19a is in close contact with the casing of the scintillation crystal. The second can 7b is moveable inside the first one. A hole 8 is arranged in the wall of the first can 7a through which a gas may be pumped in or out. The gas pressure is distributed via small holes 9 in septum 6.

If the fit between the cans 7a and 7b is gas tight the second can 7b may move like a piston inside the first one 7a when changing the gas pressure. An increase or decrease in length of the collimator tubes 10 and simultaneously a changed sensitivity and resolving power is thereby achieved. The collimator in the position shown in FIG. 2b has less sensitivity but a better resolving power than the collimator in the position shown in FIG. 2a.

The accomplishment of a movement of the second can 7b inside the first can 7a may of course be done in several different ways. Instead of the described pneumatic device it is also possible to use a purely mecanic power transmission from for example electric motors or electromagnetic pulling magnets.

The material of the partition walls 6 of the tubes should have a density that is as high as possible in order to absorb the gamma photons at angles of incidence which are not parallel or substantially parallel with the septum of the collimator tubes.

Figure 3A:
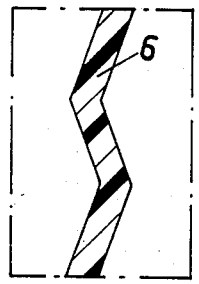
FIG. 3a is a longitudinal cut through a part of a wall.
Figure 3B:
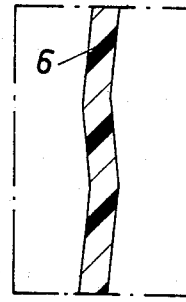
FIG. 3b is a corresponding longitudinal cut, but in this case an increased length is achieved.

As can be seen from FIGS. 3a and 3b it is possible to achieve a part of the elasticity of the septum by an accordeon-like folding of septum in the longitudinal direction. A larger density and a somewhat lower elasticity of the septum material is thereby acceptable. The difficulty of manufacturing a septum material that has a high density and at the same time good elasticity may in this way be partly eliminated.

Through the elasticity and a suitable geometrical design of the collimator tubes it is also possible to achieve a shape change of the collimator tubes. If for instance an accordion-like folding of the septum is achieved in the longitudinal direction of the collimator tubes and the points of the parts of septum which are turned against the detector 2, i.e. the scintillation crystal, are connected to a base it is possible to achieve the mentioned variations of shape of the collimator tubes.

Figure 4A:
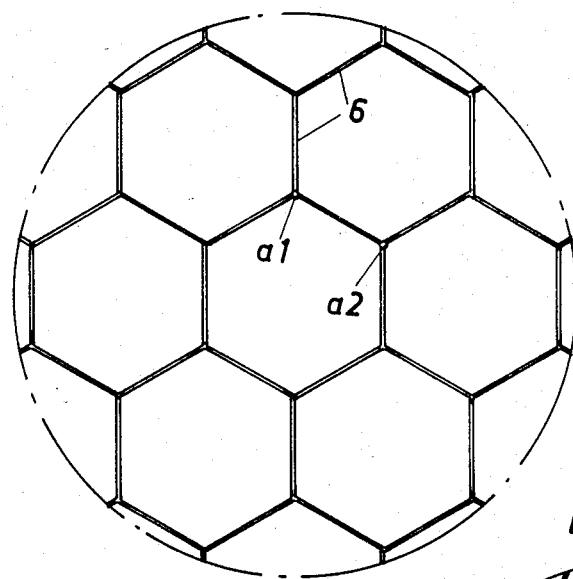
FIGS. 4a and 4b show schematically crosscuts through two different planes of a converging collimator, and FIG. 4c visualizes how the walls converge between the mentioned planes.
Figure 4B:
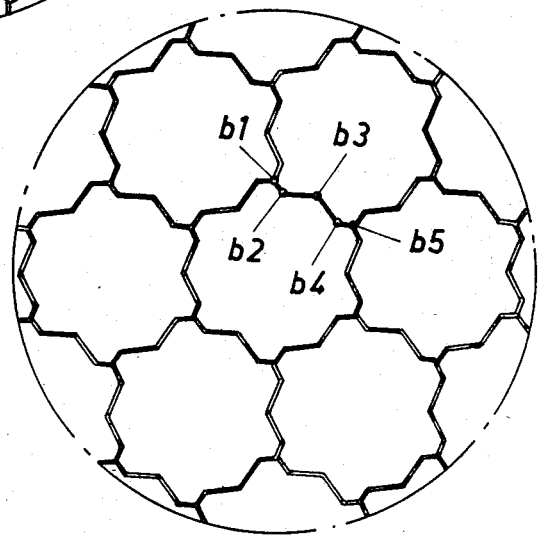
Figure 4C:
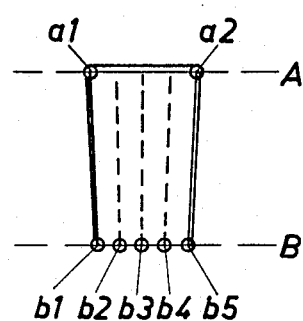

FIG. 4a shows a plane A of a collimator tube that is turned towards the detector and FIG. 4b shows a section B where the septum 6 has a possibility to move in directions in that plane. The length of the path between the points $a_1$ and $a_2$ in plane A thus equals the length of the path $b_1$, $b_2$, $b_3$, $b_4$, and $b_5$ in the plane B. FIG. 4c shows how the septum 6 converges between said planes A and B.

FIGS. 5a–b show an embodiment where the collimator 1 is shaped like a grid comprising a number of grid elements 16, which may be special designed lamellae, tubes or the like made of a high absorbing material, and arranged in a way that a great number of parallel channels are formed. The grid elements 16 are elastically conected to each other with their upper and/or lower ends so that a continuous "cake" is achieved. The elastic connection may be a layer 12 and/or 13 of silicon or the like.

Depending on whether it is desired that the collimator shall be curved in one or two dimentions the guiding means 11 must be designed for attaining the desired kind of deformation.

FIG. 5b shows a grid that is curved in one dimension where the guiding means 11 consist of slabs or ledges, which are fixed to the grid elements 16. By putting the guiding means 11 askew the grid will be curved convexly or concavely.

If a two-dimensional curving of the grid is desired the guiding means themselves must be flexible in order to distribute the curving to the grid elements 16.

It is often desired that the side of the collimator that faces the detector head of the gamma camera is kept plane, which may be achieved by using a nonelastic material for the layer 12 or 13 on the said end side. When turning the guiding means 11 only the lower end side will change its shape.

By changing a parallel tube collimator to a converging or diverging collimator respectively it is possible to obtain enough information for obtaining a three dimensional image of the examined organ without moving the gamma camera or taking pictures from different angles. This information is obtained by the fact that the farther away from the collimator a point source is situated the more its image point will be displaced in the image plane when a parallel tube collimator is changed to a converging or diverging collimator respectively. This phenomenon is illustrated in FIGS. 6a-c where $p_1$ and $p_2$ are two point radiation sources which emit gamma photons towards the collimator 1, and $p_1$ is situated at a longer distance from the collimator than $p_2$. The detection plane is called D and the detected intensity from the radiation sources $p_1$ and $p_2$ is called $B_{1a-c}$ and $B_{2a-c}$. It can be seen that the image point of $p_1$ is more laterally displaced than the image point of $p_2$ when changing the paralell tube collimator of FIG. 6a to the converging collimator of FIG. 6b or the diverging collimator of FIG. 6c.

In FIG. 7 the results obtained when summing the detected intensities $B_{1a}+B_{1b}+B_{1c}$ and $B_{2a}+B_{2b}+B_{2c}$ respectively is visualized.

The partition walls of the embodiment shown in FIG. 8 are arranged double, which makes it possible to change a parallel tube collimator to for instance a collimator with converging tubes by letting in pressurized gas or liquid in the space between the double walls. The collimator 1 thus comprises a double bottom 14, the lower partition of which comprises the lower end surface of the collimator and the upper partition of which, to which the partitions 6 are fixed, comprise connections to the space between the double partitions. The gas or liquid is let in via a connection 15 into the space in the double bottom of the collimator 14 and thereafter into the space between the double partitions, whereby these are pressed apart and the collimator tubes will obtain an area that decreases towards the lower end.

In the embodiment shown in FIGS. 9-10 the partitions of the collimator 1 are not made of elastic material. Instead the collimator comprises a large number of closely arranged grid elements, i.e. tubes 16 made of some heavy metal for example tungsten or tantalum, which are embedded in an elastic photon absorbing substance 17, e.g. rubber with an admix of heavy metal. The passages through the tubes 16 comprise the channels 10 of the collimator. Because of the elastic connection between the tubes 16 they may be displaced and the angle between them may be changed. This may for instance be achieved by arranging cavities 18 between the tubes 16 closed to one or both ends of them, whereby gas or liquid may be let into the upper or lower cavities and thereby press the tubes apart at the lower end of the collimator. The tubes will thereby diverge at the said end and convert at the opposite end.

Figure 11A:
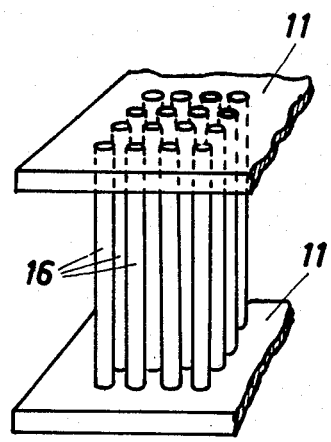
FIGS. 11 and 11b show a part of a further embodiment of a collimator according to the invention in two different positions.
Figure 11B:
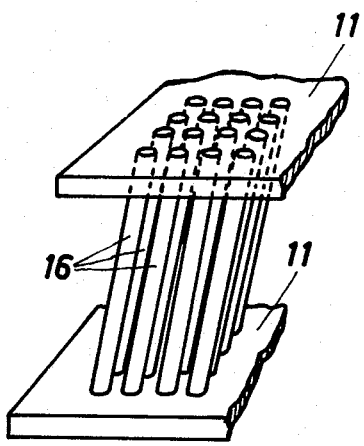

In the embodiment shown in FIGS. 11a and 11b the collimator also comprises a large number of tubes 16 made of heavy metal, which are closely arranged in a bundle of tubes. The tubes 16 are at each of their ends attached (vulcanized) to a guiding means 11, which may be in the form of a plate, by an elastic substance for example silicon rubber.

The slope of the tubes 16 and thereby the slope of the collimator channels is changed according to FIG. 11b by a lateral displacement of the slabs 11 relative to each other. The position of the image point or its relative position in the detection plane is thereby changed, and this information can be used for a calculation of the distance of the object (i.e. the radiation source) to the collimator.

If the tubes 16 are connected to an elastic slab 11 only at one end and the other end is free it is possible to achieve a ray-formed scattering of the tubes, i.e. the collimator channels or, directing these towards each other, by curving the plate upwards.

Figure 12:
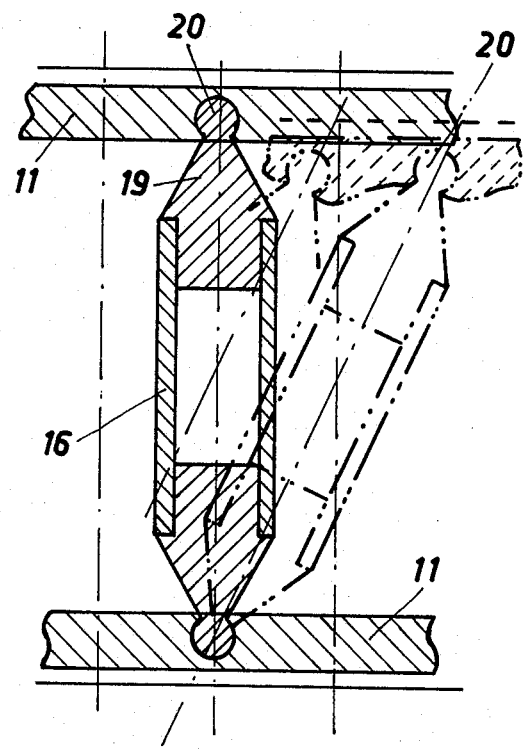
FIG. 12 shows in a larger scale a modified embodiment of the collimator shown in FIG. 11.

Instead of the flexible connection of the tubes 16 it is also possible to connect these pivotably to the guiding means 11. This can be done by providing the tubes 16, which are made of high absorbing material, with transferring means 19 means of a low absorbing material at the ends, said means comprising a ball joint 20, that is journalled in the guiding means, i.e. the plate, 11 as shown in FIG. 12.

Figure 13:
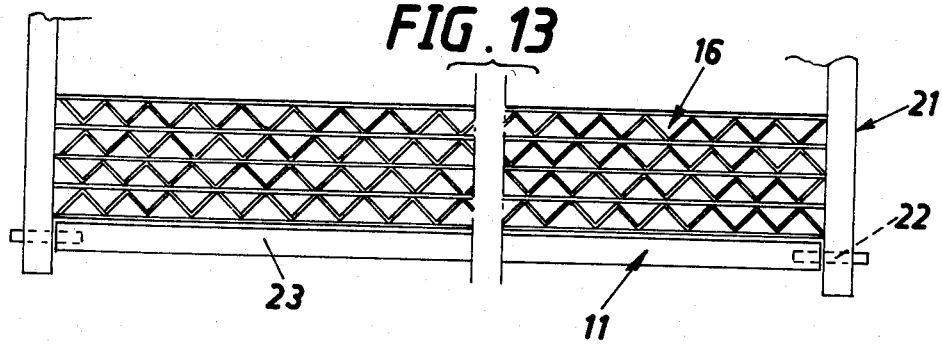
FIG. 13 shows a part of a lamellar collimator in wiew from above.
Figure 14:
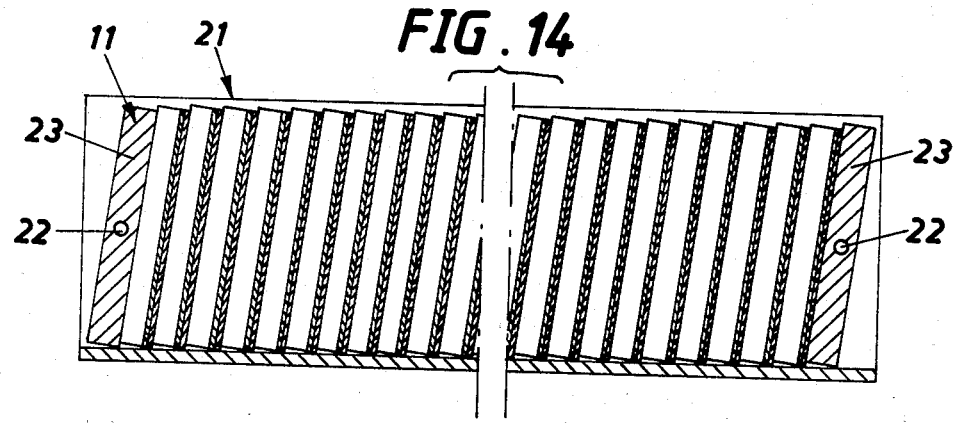
FIG. 14 shows a cut through the lamellar collimator of FIG. 13.

In another embodiment shown in FIG. 13 the grid elements 16 consist of corrugated lamells made of for example lead sheets, which are placed upended in a box-formed container 21 with two fixed and two movable side walls 23 which thus are pivotable around a pivot axis 22, and which constitute the guiding means 11. By sloping these more or less from the vertical position the collimator channels which are made up of the corrugated lamells will synchronously occupy different angles. Each lamell consists of a sheet 24 that is corrugated in cross-cut and between these are arranged free flat sheets 25 which may be made of a high or low absorbing material depending on the desired area and form of the collimator channels. The flat sheet may also form a unity together with the corrugated sheet 24.

Figure 15:
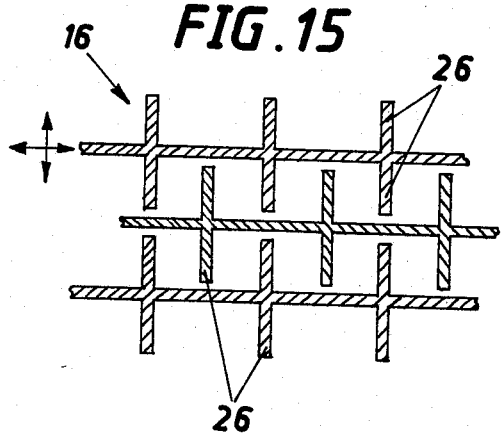
FIG. 15 shows another embodiment of a lamellar collimator in wiew from above.

The corrugation may be formed in many different ways, and also so that an increase or a decrease of the area of the collimator channels is achieved. Such an embodiment is shown in FIG. 15, where the lamells 16 are formed with transverse flanges 26 which are spaced apart a distance corresponding to the double flange length. The flanges of the neighboring lamells are situated in the space between the flanges 26 and by displacing the lamells sidewards the free space therebetween may be changed, i.e. the area of the collimator channels may be made variable.

It is of course possible to achieve a change of the length of the collimator channels, shape, dimension and slope in a number of other ways than the above described. It is also possible to achieve a collimator by using the described technique in which partly the length of the channels and partly their shape or slope respectively may be changed.

The collimator may be curved in one dimension or two dimensions.

The center of curving may be displaceable relative to the geometric axis of the collimator, e.g. by dividing the collimator into sections, which are separately pneumatic or hydraulic affectable. It is for example possible to let the collimator converge against a point that is not at the geometrical axis of the collimator. This is of great value since the examined organ or part of the organ is not always situated on the mentioned axis. If the collimator channels should be parallel the grid elements may be made of a solid high absorbing material.

I claim:

1. A collimator placed between a radiation source and a radiation sensitive medium, comprising: a plurality of lamellae having partitions extending in spaced, parallel relationship to each other, each lamella also having a plurality of spaced flanges extending transverse to said partitions, adjacent partitions and flanges defining therebetween collimator apertures of a certain size in a plane perpendicular to said flanges and partitions, at least one lamella being movable with respect to adjacent lamellae in said plane transverse to said partitions such that the size of the collimator apertures between said movable and adjacent lamellae can be changed.

2. A collimator placed between a radiation source and a radiation sensitive medium, comprising: a plurality of lamellae having partitions extending in spaced, parallel relationship to each other, each lamella also having a plurality of spaced flanges extending transverse to said partitions, adjacent partitions and flanges defining therebetween collimator apertures of a certain size in a plane perpendicular to said flanges and partitions, at least one lamella being movable with respect to adjacent lamellae in said plane parallel to said partitions such that the size of the collimator apertures between said movable and adjacent lamellae can be changed.

3. A collimator placed between a radiation source and a radiation sensitive medium, comprising: a plurality of lamellae having partitions extending in spaced, parallel relationship to each other, each lamella also having a plurality of spaced flanges extending transverse to said partitions, adjacent partitions and flanges defining therebetween collimator apertures of a certain size in a plane perpendicular to said flanges and partitions, at least one lamella being movable with respect to adjacent lamellae in said plane parallel to and transverse to said partitions such that the size of the collimator apertures between said movable and adjacent lamellae can be changed.

* * * * *